United States Patent [19]

Arp et al.

[11] Patent Number: 4,643,303
[45] Date of Patent: Feb. 17, 1987

[54] MODULAR STERILIZING SYSTEM

[75] Inventors: Robert A. Arp, Eden Prairie; W. Patrick Conroy, Minneapolis; Curtis H. Miller, Burnsville; James M. Weinzetl, Mahtomedi, all of Minn.

[73] Assignee: Micromedics, Inc., St. Paul, Minn.

[21] Appl. No.: 787,787

[22] Filed: Oct. 15, 1985

[51] Int. Cl.$^4$ .................... A61L 2/26; B65D 81/18
[52] U.S. Cl. ................................ 206/370; 206/438; 422/300
[58] Field of Search ............. 206/363, 369, 370, 438, 206/439, 564; 422/300, 301, 310, 302; 211/70.6

[56] References Cited

U.S. PATENT DOCUMENTS

| 3,697,223 | 10/1972 | Kovalcik et al. | 206/370 |
| 3,890,096 | 6/1975 | Nichol et al. | 206/564 |
| 3,925,014 | 12/1975 | Langdon | 206/370 |
| 4,050,894 | 9/1977 | Genis | 206/363 |
| 4,135,868 | 1/1979 | Schainholz | 206/438 |
| 4,342,391 | 8/1982 | Schainholz | 206/370 |
| 4,541,992 | 9/1985 | Jerge et al. | 422/310 |

FOREIGN PATENT DOCUMENTS

| 2207339 | 9/1973 | Fed. Rep. of Germany | 422/300 |
| 2839219 | 3/1980 | Fed. Rep. of Germany | 206/439 |
| 0451051 | 2/1913 | France | 422/301 |

Primary Examiner—William Price
Assistant Examiner—Jimmy G. Foster
Attorney, Agent, or Firm—Orrin M. Haugen; Thomas J. Nikolai

[57] ABSTRACT

A surgical instrument storage and transporting assembly which facilitates the sterilization, storage, protection, handling and presentment during surgery of a variety of surgical instruments and devices. An outer box-like enclosure having a removable top, contains a wire basket in which are placed a plurality of instrument carrying modules. The individual modules are provided with an instrument gripping member which positively, but releasably, holds the instruments in a first predetermined order and orientation when being stored in the box-like enclosure, but which permits placement of the instruments in the same order, but in a second orientation to facilitate the location and selection of given instruments during the course of a surgical procedure when the modules have been removed from the basket and placed on the surgical stand. When the instruments, instrument modules and basket are placed in the enclosure and covered with the removable top, the entire unit can be put in an autoclave and subjected to sterilizing steam which, because of the proper attention to hole patterns in the enclosure, the modules and the instrument supports, a free flow of steam takes place to ensure total sterilization. Because the individual instruments are positively held, they do not become loose and scrambled even during rough handling.

4 Claims, 5 Drawing Figures

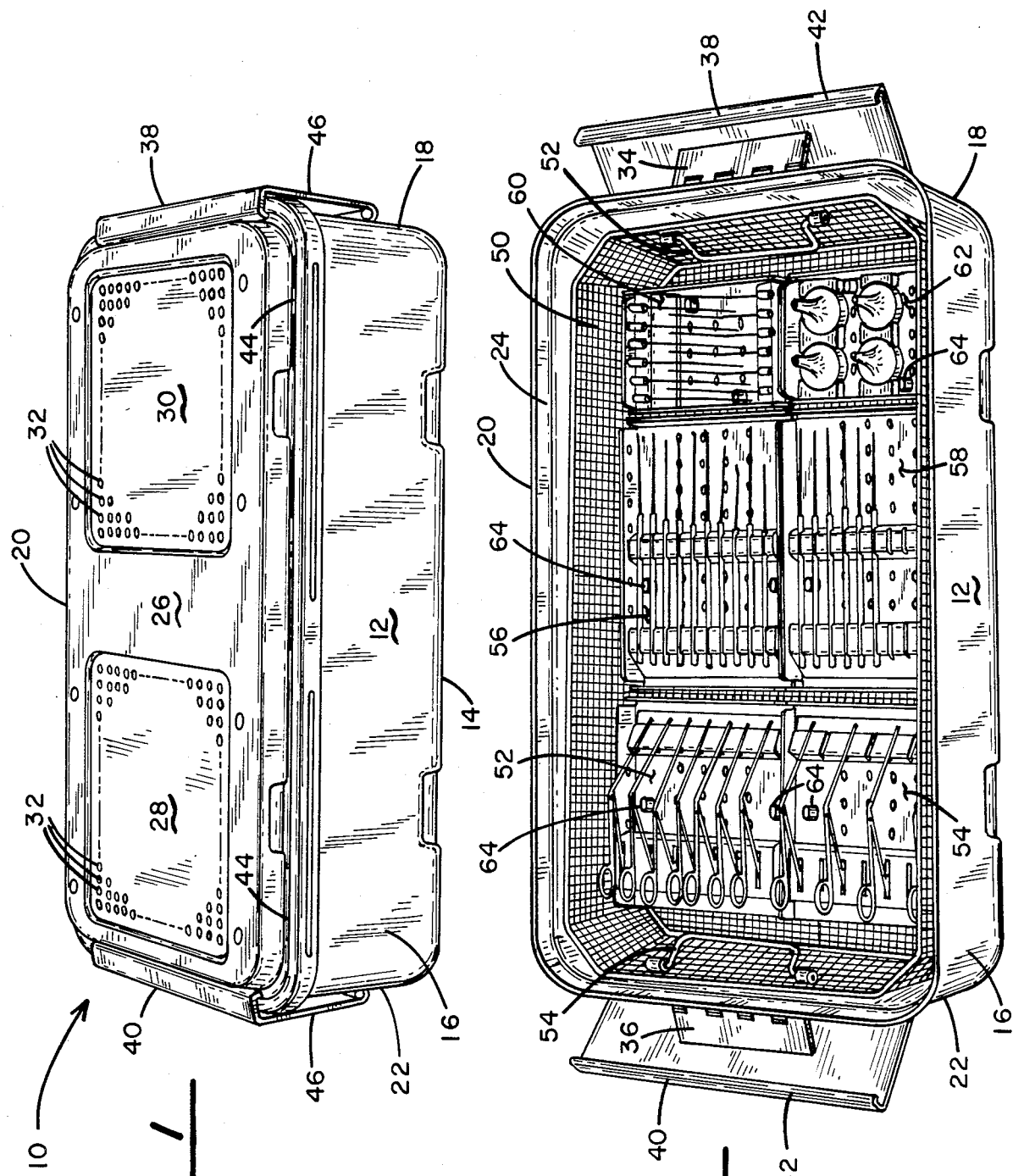

MODULAR STERILIZING SYSTEM

BACKGROUND OF THE INVENTION

I. Field of the Invention

This invention relates generally to materials handling apparatus, and more particularly to an integrated design of an assembly for facilitating sterilization, storage, transport and presentment of surgical instruments.

II. Discussion of the Prior Art

Over the past decade or so there has been a trend in surgical medicine to use disposable intruments following a single use. Commonly, such single-use instruments come from the manufacturer in a sterile kit which is only opened once the surgical procedure has begun and, once used, is thrown away. There are many instruments, however, that because of their intricate construction and precision manufacture are of a cost which precludes the disposal thereof following a single use. For example, in the field of microsurgery otolaryngology, specialized instruments have been developed for conducting surgery on various organs. For example, in otolaryngology, a range of middle ear instruments have been developed for repair and reconstruction of the bones and tissue of the middle ear of a patient. The middle ear instruments, including forceps, scalpels, scissors, picks, hooks, currettes, specula and micro-suction tips, used in these delicate areas are generally of high precision and come in a variety of types, shapes and sizes, all of which may be used during a particular surgical procedure. For example, considering only forceps, they come straight, left curved, right curved, serrated, cupped, etc.

In the past, after surgery, it has been the practice to co-mingle all of these instruments in a basket which is then placed within an autoclave and subjected to sterilizing steam. When ready for use, a surgical nurse would take the instruments from the autoclave basket and lay them out on a Mayo stand in a particular arrangement dictated by the surgeon so that they would be within convenient reach of the surgeon or his surgical nurse.

The co-mingling of the instruments in loose fashion in a basket and the transportation thereof has had the tendency to damage them, rendering them unusable. There is no way to organize them and to protect them at the same time. This, of course, increases the cost of the particular procedure.

In many instances, the surgical instruments used in various procedures look very much alike and differ only in minor respects, such as size, angle of bend, tip type, etc. At a glance, it is difficult to discern one instrument from another and, therefore, the surgical nurse or operating surgeon may have a difficult time selecting the right instrument to use at any given time, especially when it is considered that they are generally arrayed side-by-side on the Mayo table in an order laid out before surgery by the nurse preparing for the procedure. It is, of course, imperative that the surgeon be able to rapidly identify and select the appropriate instrument to be used at any given time without confusion and without any undue lapse of time.

The problem has been that there has been nothing designed to both protect and organize the delicate instruments and to incorporate them into one pan along with the larger instruments and not damage them. The optimum arrangement for the nurse would be to be able to put all the instruments (both delicate and gross) needed to do, for example, a middle ear procedure in one container where they would be protected and organized. When this protective container is opened, it would be desirable if the instruments then could be effectively "presented" to the Mayo stand.

SUMMARY OF THE INVENTION

The present invention is intended to obviate most of the problems inherent in the prior art sterilizing, storage, transportation and presentment of reusable surgical instruments. During the surgical procedure, the instruments are arranged on a plurality of individual modules, with instruments of a given type being confined to the same module. The modules are formed from metal or plastic sheets which are perforated and which include one or more resilient, rubber-like bars or ribs having recesses formed therein for positively gripping and holding an instrument at a desired disposition, making them easy to identify and select during the course of the procedure. Following use, the instruments may be returned to the recess in the instrument holding bar from which they were originally taken and all of the instruments on a given modular unit be moved to an orientation in which they present a lower profile. The individual modules are especially designed to fit into a wire basket which is provided with locating pins or studs passing through the modular units to releasably but positively hold them while they are being transported within the basket. The basket may be placed within a box-like enclosure having a removable top, which top can be clamped in position with respect to the base to form an enclosure. The major surface of the enclosure top is provided with a pattern of apertures which allows the ready flow of steam or other sterilizing fluids through the interior of the enclosure. Because the individual modules within the wire basket are also provided with a series of holes, the sterilant is able to reach the interior cavities of the flexible instrument holding bars as well as the instruments themselves during the sterilization procedure.

Because the individual instruments are firmly gripped by the resilient instrument holding bars on each of the modular units, they are prevented from becoming intermixed nor do they come in contact with one another during transportation and handling, thus prolonging the lives of the instruments.

OBJECTS

It is accordingly a principal object of the present invention to provide an improved materials handling system for surgical instruments.

Another object of the invention is to provide a plurality of modules, each of which is especially designed to contain instruments of a given variety wherein the modules contain means for effectively presenting the instruments to the surgeon or nurse during use.

A still further object of the invention is to provide a materials handling system for surgical instruments in which the instrument modules are designed to fit into a carrying basket in a fixed, stable orientation.

Yet another object of the invention is to provide a materials handling system for surgical instruments in which the aforementioned basket containing the instrument bearing modules is designed to fit within an outer housing or container and wherein passages are provided in the housing or container and in the modules themselves to permit the free flow of sterilizing fluids in and around the instruments and the modules supporting those instruments.

These and other objects and advantages of the invention will become apparent to those skilled in the art from the following detailed description of a preferred embodiment, especially when considered in conjunction with the accompanying drawings in which like numerals in the several views refer to corresponding parts.

DESCRIPTION OF THE DRAWINGS

FIG. 1 is a perspective view showing the box-like enclosure with its top clamped in place;

FIG. 2 illustrates the enclosure of FIG. 1 with the top removed so as to reveal the contents thereof;

DESCRIPTION OF THE PREFERRED EMBODIMENT

Figure 3:
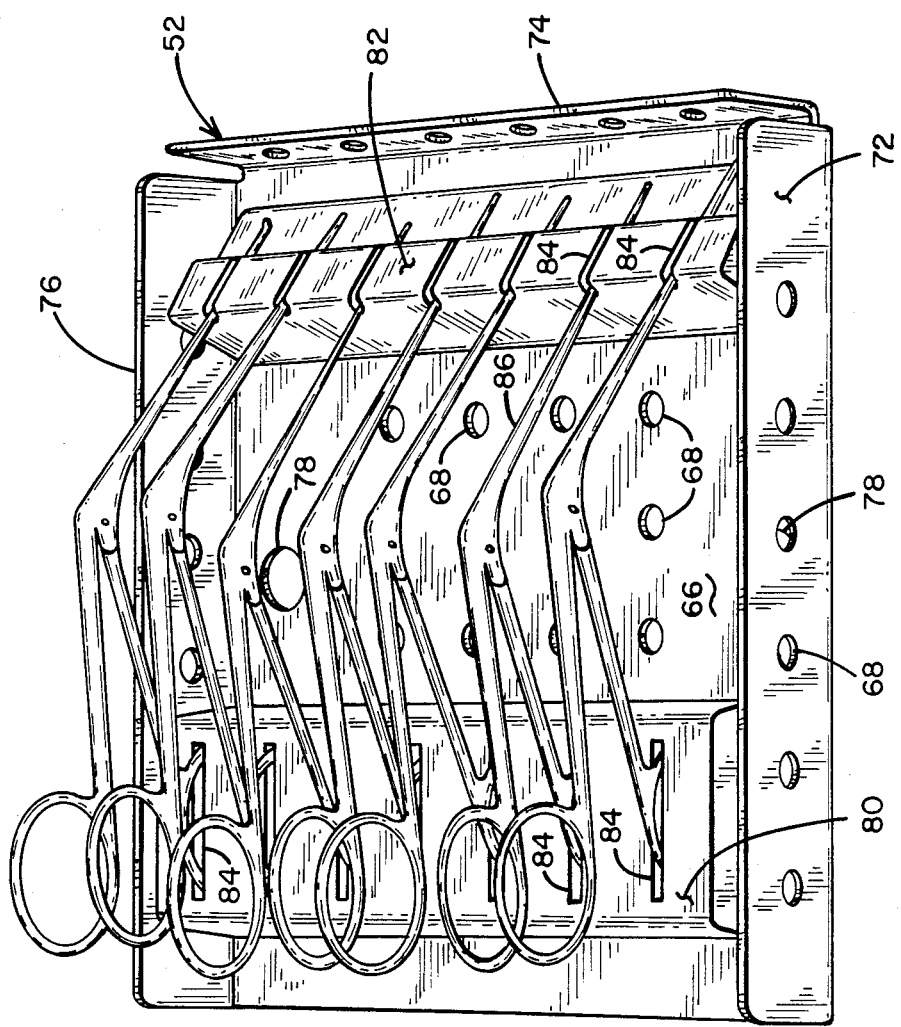
FIG. 3 illustrates one of a plurality of different instrument holding modules contained within the carrying basket in FIG. 2.

Certain terminology will be used in the following description for convenience in reference only and should not be construed as limiting. The words "upwardly", "downwardly", "rightwardly" and "leftwardly" will refer to directions in the drawings to which reference is made. The words "inwardly" and "outwardly" will refer to directions toward and away from, respectively, the geometric center of the device and associated parts thereof. This terminology is intended to include the words specifically mentioned above, derivatives thereof as well as words of similar import.

Referring to FIG. 1, there is indicated generally by numeral 10 the box-like housing or enclosure in which surgical instruments may be sterilized, transported and stored for later use. The enclosure comprises a box-like base 12 having a bottom surface 14 and four generally perpendicular, upwardly projecting, continuous side walls including a front side wall 16, a right side wall 18, a rear side wall 20 and a left side wall 22.

As can best be seen in FIG. 2, the side walls 16–22 define a generally open top and the upper perimeter of all four side walls is rolled to define an upwardly projecting lip 24. Referring to FIG. 1 again, arranged to seal the open top of the base 12 is a top member or cover 26 having generally planar areas 28 and 30 having a plurality of apertures 32 arranged in rows and columns which, as will be further explained, permit the ingress and egress of steam or other gaseous sterilants. Referring again to FIG. 2, it can be seen that attached to the end walls 18 and 22 are hinges 34 and 36 which attach to clamp members 38 and 40. The clamp members have a rolled top edge surface 42 which is curved to engage a U-shaped depression 44 formed about the periphery of the top member 26. Thus, the overhand clamps 38 and 40 serve to releasably hold the cover 26 in its closing relationship relative to the open top of the base portion 12. Also attached at opposed ends of the base portion of the enclosure are swing-away handles 46 which may facilitate the lifting and carrying of the container 10.

Referring again to FIG. 2, it can be seen that there is disposed within the base portion 12 of the enclosure 10 a wire basket 50 which is generally of the same shape as the enclosure 12 but of a smaller length, width and height dimension to permit the basket 50 to be fully contained within the base 12. Attached at each end of the basket 50 are further handles 52 and 54 which facilitate the lifting of the basket into and out from the box-like base portion 12. Containers of enclosures of the above-described type including the basket arrangement are commercially available from one or more companies, including Genesis, Inc. of Cleveland, Ohio, Instrumed, Inc. of Kirkland, Wash., and Amscro, Inc. of Erie, Penna.

The basket 50 is arranged to support a plurality of individual instrument modules 52, 54, 56, 58, 60 and 62, for example. In illustrating the invention, the modules are shown as containing instruments useful in the conduct of otolaryngological procedures with the modules 52 and 54 being used to firmly support forceps and scissors of various size, shape and tip styles, modules 56 and 58 holding various picks and currettes, the module 60 containing suction tips and the modular unit 62 containing specula. Those skilled in the art can appreciate, however, that other instruments may be arrayed in a like fashion and it is not intended that the invention be limited only to the field of otolaryngology.

With continued attention to FIG. 2, there can be seen projecting through apertures formed in the individual modules a plurality of upwardly projecting studs 64. These studs are attached to the bottom surface of the basket 50. They serve to lock the tray-like modules 52–62 in position and to prevent them from shifting laterally within the container so long as the container is not actually inverted.

Referring next to FIG. 3, there is shown the details of construction of the module 52 of FIG. 2. It is seen to comprise a generally flat base sheet 66 which has regularly spaced rows and columns of apertures 68 formed therethrough. Three of the four peripheral edges of the sheet 66 are turned up at a 90° angle to form upwardly extending side walls 72, 74 and 76 which, like the base portion 66, includes a pattern of apertures 68. At predetermined locations corresponding to the positioning of the studs 64 (FIG. 2) on the bottom of the basket 50 are holes 78 of somewhat larger diameter than the holes 68. This allows the module 52 to slip onto the studs 64 in a manner shown in FIG. 2.

Affixed to the upper surface of the sheet 66 when viewed in FIG. 3 are instrument retaining bars 80 and 82. These bars or wedges are preferably made from a resilient, compressible, plastic, rubber-like material, such as silicone rubber, and are provided with a series of parallel recesses 84 into which portions of the instruments 86 may be inserted and frictionally engaged by the compressible material from which the bars 80 and 82 are fabricated.

The aligned slots 84 in the spaced-apart instrument support bars 80 and 82 maintain the instruments in an organized, parallel relationship. While not shown in FIG. 3, it is also possible to place identifying legends along the various recesses 84 to identify the type of instrument to be placed in that recess during loading of the modular units.

In FIG. 3, the instruments are shown in their disposition in which they would be stored in the basket 50 of FIG. 2. The slots 84 in the instrument holding bar 80 are configured, however, so that the instrument may be rotated counterclockwise from the disposition illustrated so that the tip ends of the instruments swing out of the recesses 84 in the holding wedge 82 and point generally upward so as to be fully viewable by the surgeon and/or the surgeon's assistant but while still being retained in the instrument holding bar 80 on the module 66.

While not shown in FIG. 3, there is associated with each of the slots 84 in the instrument holding bars 80 and 82 a vertically extending bore which communicates with the slots 84 and with ones of the perforations 68 located on the tray-like base sheet 66 of the module 52. Thus, when the module 52 is positioned within the basket 50 and steam or another gaseous sterilant is made to flow through the apertures 32 formed in the lid 26 of the enclosure 10, it permeates the entire interior of the enclosure and can pass up and around the instruments positioned in their holding bars 80 and 82, thus ensuring effective sterilization.

Figure 4:
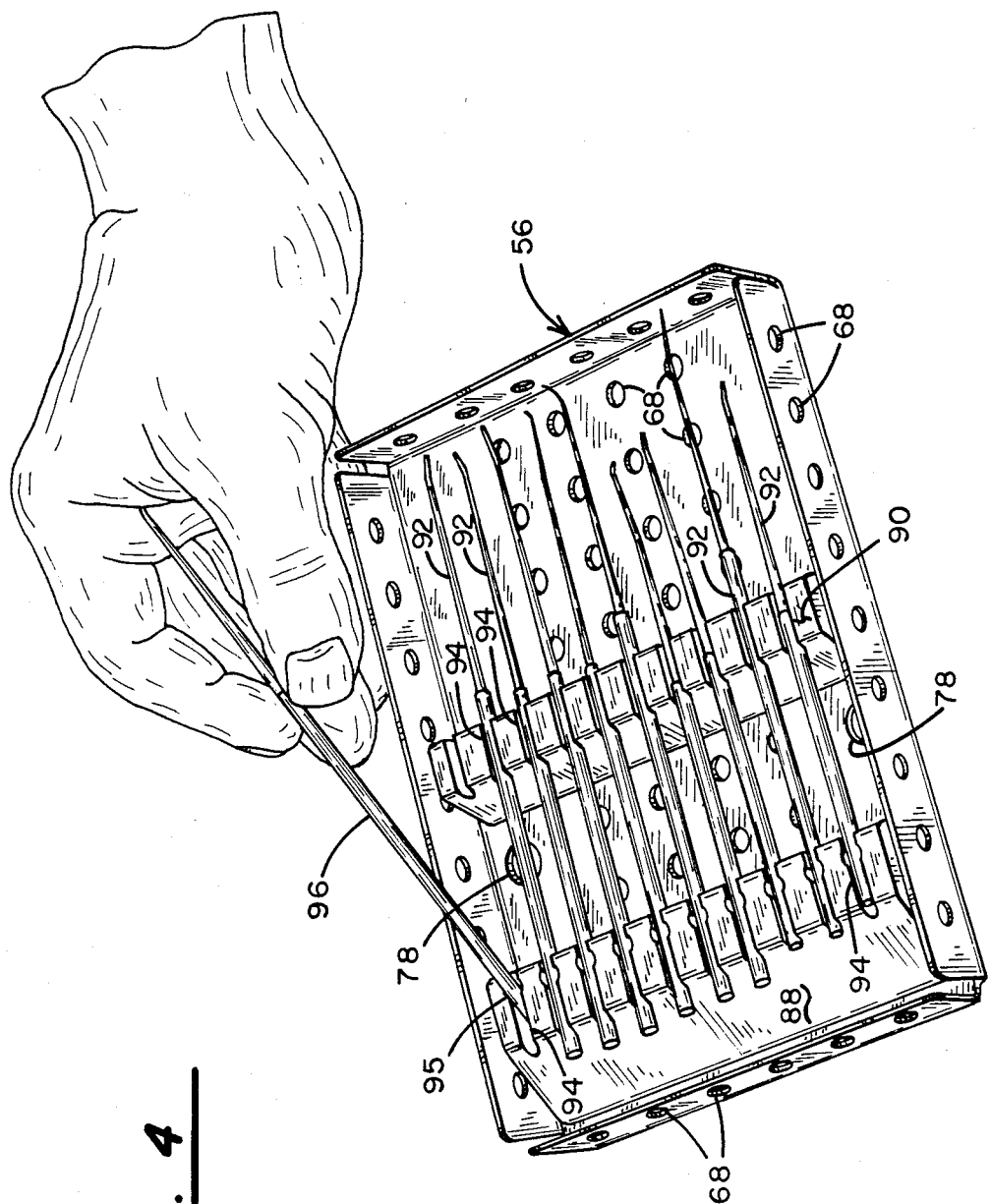
FIG. 4 illustrates the manner in which a surgical instrument can be positioned in its module for ease of identification and grasping during a surgical procedure.

FIG. 4 is a perspective view of the module 56, but removed from the basket 50. It too is of a construction quite similar to that of the module 52 shown in FIG. 3 but its instrument holding bars 88 and 90 are configured to hold forceps of various sizes and tip configurations. The curettes 92 may have various tip configurations and are retained within aligned recesses 94 formed in the compressible rubber-like instrument holding bars 88 and 90 in their low-profile orientation in which they are held when stored or when being sterilized. Formed in the base of the recesses 94 in the instrument support bar 88 are a plurality of bores 95 which extend at a predetermined acute angle with respect to the base of the modular unit 56. These bores are of a diameter which permit the handles of the picks or currettes to be inserted therein as illustrated by the pick 96. Prior to surgery, the instruments are so inserted in the bores of the instrument retaining bar 88 so that they will be elevated and more readily viewed and grasped by the surgeon during the course of the surgical procedure. Thus, rather than rolling around loose in the surgeon's instrument table, the instruments are positively retained at a precise location and at a desired presentment angle.

Again, enlarged apertures 78 can be seen in the bottom surface of the module 56 and it is through these enlarged apertures 78 that the studs 64 (FIG. 2) project when the modules are disposed in the basket 50.

The same bores which are formed in the instrument holding bar 88 to retain the instrument in an elevated, angulated position also provide a passage through which the steam or other sterilant gas may flow to ensure that all exposed surfaces are treated with the sterilant. Similar bores are formed through the thickness of the instrument holding bar 90 in FIG. 4 to provide a sterilant passage through the aligned apertures in the base of the module and the instrument holding groove 94 in the bar 90.

Figure 5:
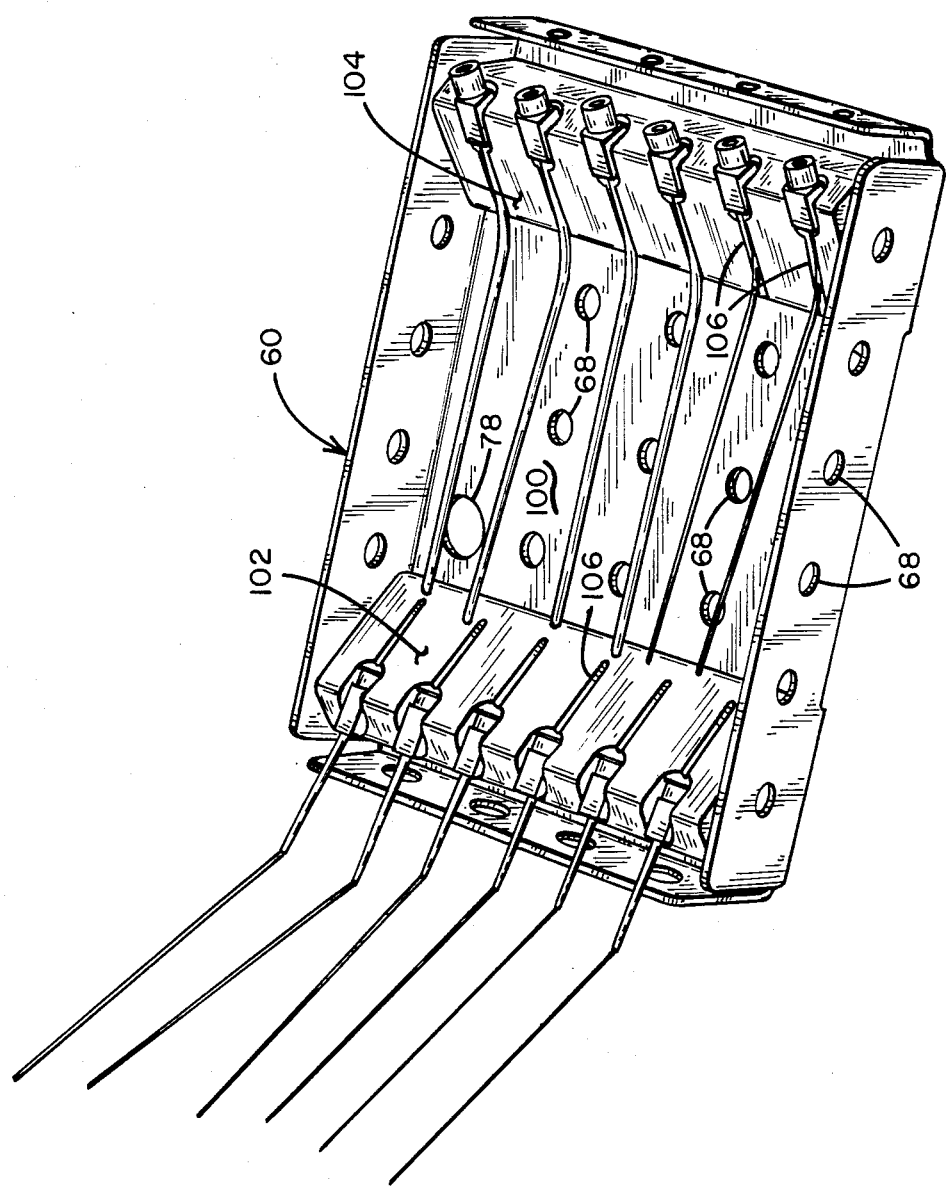
FIG. 5 illustrates a further surgical module in which half of the instruments are arrayed in their low-profile position while the other half are arrayed for presentation to the surgeon.

FIG. 5 is a perspective view showing the modular unit 60 in FIG. 2. Like the modules previously described, the modular unit 60 has a bottom surface 100 though which pass a plurality of apertures 68 (FIG. 3) and the bottom surface 100 has its peripheral edges upturned to form four side walls. Contained within the module at spaced apart locations therein are instrument retaining bars 102 and 104 which are preferably molded from Silastic or other autoclavable rubber-like material. During molding, the bars 102 and 104 have formed therein a plurality of parallel, aligned recesses dimensioned so as to firmly grip the suction tips which the modular unit 60 is intended to hold.

The suction tips contained within the recesses 106 of the instrument holding bar 104 are disposed in the orientation they would have during sterilization and/or storage when contained within the basket and within the outer enclosure 10. The instrument support bar 102 contains similar suction tips but oriented as they would be during a surgical procedure which allows size markings to be readily viewed and the instrument easily grasped and removed from the modular modular unit 60.

Although not shown in FIG. 5, the recesses formed in the instrument support bars 102 and 104 are in communication with apertures 68 formed in the base 100 of the module via bores formed vertically through the material comprising the support bars 102 and 104 so as to permit the ready flow of sterilant therethrough.

Upon completion of the surgical procedure, a responsible person such as the surgical nurse or assistant would be expected to return all of the instruments to their appropriate module and recess but with all instruments aligned in their low-profile orientation. The modules would then be positioned in the basket with the studs passing through the appropriate apertures in the base of the module to prevent their lateral shifting within the basket. The basket is then inserted within the base portion 12 of the outer housing or enclosure and the top or lid 26 is positioned to cover the enclosure while the clamps 38 and 40 are manipulated to latch the cover in place. Thus, all of the instruments, organized in their modules may be carried as a unit from the operating room and then stored prior to re-sterilization and reuse at a later time.

While there has been shown and described a preferred embodiment of the invention, those skilled in the art may arrive at modifications and changes which really do not depart from the spirit and scope of the invention. Thus, in assessing the scope of the invention, reference is to be made to the following claims.

What is claimed is:

1. An autoclavable surgical tray storage and transporting assembly, comprising:
    (a) a fluid impervious box-shaped base having a bottom surface and four mutually perpendicular side walls extending upwardly therefrom to define an open top;
    (b) a generally rectangular top member having means for receiving the upper edges of said four side walls defining said open top, said top member having a pattern of perforations extending through the major surface thereof by which steam can enter;
    (c) means for clamping said top member to said base;
    (d) a removable wire basket having a bottom and four upwardly projecting, mutually perpendicular sides, the length, width and height dimensions of said basket allowing it to fit within said box-shaped base;
    (e) a plurality of instrument modules removably situated in said wire basket, each of said modules supporting in a predetermined orderly manner, instruments to be used in carrying out surgical procedures, said instrument modules each comprising a generally flat, rectangular sheet having its peripheral edges formed normal to the plane of said flat sheet, said sheet having a pattern of apertures therethrough and at least one flexible, deformable, plastic instrument supporting member on said sheet, said instrument supporting member including a recess dimensioned to receive a surgical instrument therein with a predetermined gripping force; and (f) means for releasably securing said instrument modules to said bottom of said basket.

2. The assembly as in claim 1 wherein said instrument supporting member includes a passage extending between one or more of said apertures on said sheet and said recess.

3. The assembly as in claim 1 and further including a further flexible, deformable, plastic instrument supporting member on said sheet and including means for presenting a surgical instrument in a desired orientation during a surgical procedure.

4. The assembly as in claim 1 wherein said sheet, said peripheral edges and said instrument supporting member are integrally formed in a molding process.

* * * * *